United States Patent
Calvani

(10) Patent No.: US 8,053,472 B2
(45) Date of Patent: Nov. 8, 2011

(54) USE OF THE ACETYL L-CARNITINE IN ASSOCIATION WITH THE BIOTIN FOR THE TREATMENT OF PATIENTS WITH TYPE 2 INSULIN-RESISTANT DIABETES MELLITUS

(75) Inventor: Menotti Calvani, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 449 days.

(21) Appl. No.: 12/216,279

(22) Filed: Jul. 2, 2008

(65) Prior Publication Data

US 2008/0269307 A1 Oct. 30, 2008

Related U.S. Application Data

(63) Continuation of application No. 10/478,372, filed as application No. PCT/IT02/00338 on May 24, 2002, now abandoned.

(30) Foreign Application Priority Data

May 29, 2001 (IT) .............................. RM2001A0294

(51) Int. Cl.
*A61K 31/205* (2006.01)
(52) U.S. Cl. .................. 514/554; 514/555; 514/556
(58) Field of Classification Search .................. 514/556, 514/554, 555
See application file for complete search history.

(56) References Cited

U.S. PATENT DOCUMENTS

| 4,751,242 A | 6/1988 | Calvani et al. |
| 5,929,066 A | 7/1999 | McCarty |
| 6,020,139 A | 2/2000 | O'Day et al. |

FOREIGN PATENT DOCUMENTS

EP 0 591 857 4/1994

OTHER PUBLICATIONS

McCarty, "Toward Practical Prevention of Type 2 Diabetes", Medical Hypotheses, Eden Press, vol. 54, No. 5, May 2000, pp. 786-793.

*Primary Examiner* — Yong Chong
(74) *Attorney, Agent, or Firm* — Lucas & Mercanti LLP

(57) ABSTRACT

The invention relates to the use of the acetyl L-carnitine in association with the biotin for the treatment of patients with Type 2 insulin-resistant diabetes mellitus.

3 Claims, No Drawings

USE OF THE ACETYL L-CARNITINE IN ASSOCIATION WITH THE BIOTIN FOR THE TREATMENT OF PATIENTS WITH TYPE 2 INSULIN-RESISTANT DIABETES MELLITUS

This application is a continuation application of Ser. No. 10/478,372 filed Nov. 21, 2003 now abandoned, which in turn is a U.S. national phase of International Application PCT/IT02/00338 filed May 24, 2002, which designated the U.S., which in turn claims priority of Italian application Serial No. RM2001A000294 filed May 29, 2001, the entire contents of each of which are hereby incorporated by reference.

The present invention relates to the use of acetyl L-carnitine in association with biotin for the treatment of patients suffering from Type 2 insulin-resistant diabetes mellitus.

The diabetes mellitus is a syndrome resulting from the interaction of hereditary and environmental factors; it is characterized by abnormal insulin secretion and other metabolic and vascular abnormalities resulting in elevated concentration of glucose in the blood, non-specific accelerated arteriosclerosis, neuropathy and thickening of the capillary basal lamina which causes a degeneration of the kidney and the retina.

According to a modern classification, the diabetes is divided into two main categories:

1—Insulin-dependent diabetes mellitus (also known as Type 1 diabetes) which concerns patients suffering from this type of diabetes who literally depend on exogenous insulin to prevent ketoacidosis and death. As far as the endogenous insulin secretion is concerned, patients suffering from Type 1 diabetes mellitus exhibit insulinopenia.

2—Noninsulin-dependent diabetes mellitus (also known as Type 2 diabetes); patients with this type of diabetes do not need insulin to live: they can decide whether to use it or not to control the symptoms of the diabetes. As far as the endogenous insulin secretion is concerned, patients with Type 2 diabetes can be further classified into two groups. In the first group, insulin levels are either normal or lower than normal; in the second group, insulin values are higher than normal and patients exhibit insulin resistance.

The Type II diabetes is currently treated with oral antidiabetes medicaments, which exert a positive action both on insulin resistance, i.e. the glitazones and on the altered insulin secretion, i.e. the sulfonylureas.

Despite being very useful, these compounds present some disadvantages due to their toxicity (Pharmacol. Res. 1994 October-November; 30(3):187-228; Drug. Saf. 1994 October; 11(4):223-41).

Previous therapeutic uses of acetyl L-carnitine for the treatment of diabetes are already known.

For example, WO 98/01128 discloses the use of the acetyl L-carnitine, isovaleryl L-carnitine, propionil L-carnitine to increase the levels of IGF-1. The diabetes is also included in the long list of curable pathologies stated in WO 98/01128.

WO 98/41113 describes a therapeutic nutritive composition for patients with diabetes mellitus consisting of gamma-linolenic acid, acetyl L-carnitine, mineral salts and vitamins.

U.S. Pat. No. 4,362,719 describes the use of the L-carnitine and the acyl L-carnitine in treating the juvenile onset diabetes mellitus.

U.S. Pat. No. 5,430,065 describes the use of the L-carnitine and the acyl L-carnitine in the long-term treatment of those patients with noninsulin-dependent diabetes.

U.S. Pat. No. 5,430,065 describes some orally administrable nutritive compositions, which consist of a mixture of vitamins, amino acids, mineral salts, plant extracts, neuro-chemical precursors, enzymes, and pH regulators. The biotin and the acetyl L-carnitine are also mentioned in the long list of compounds.

U.S. Pat. No. 6,149,924 describes cosmetic compositions for topic use, consisting of the association of amino acids, enzymes, hydroxy acids and various other compounds. Both biotin and acetyl L-carnitine are also mentioned in said patent.

None of the above-cited prior art documents describe or suggest the use of biotin in association with acetyl L-carnitine for the treatment of the Type 2 insulin-resistant diabetes mellitus.

The acetyl L-carnitine, a product available on the market, can be prepared by following the method described by R. Krinmberg, and W. Wittandt, in Biochem., Z. 251, 229 (1932).

Previous uses of the biotin in treating the diabetes are also known.

For example, McCarty M F., in Med. Hypotheses 1999; May; 52(5):401-6 reports that high doses of biotin in association with chromium picolinate are useful for the therapeutic treatment of the Type 2 diabetes.

Zhang H, Osada K, Maebashi M, Ito M, Komai M, Furukawa Y., in J. Nutr. Sci. Vitaminol. (Tokyo) 1996; December; 42(6):517-26 reports that the altered tolerance to glucose improves when high doses of biotin are added to the diet of hypertriglyceridemic rats with noninsulin-dependent diabetes mellitus.

The biotin can be also prepared by following the method described by Harris et al., in J. Am. Chem. Soc. 67, 2096. (1945) and is however available on the market.

Despite the remarkable progress made by the research in recent years in finding new medicaments useful for the treatment of the Type 2 diabetes, there is still a great need for new compounds or associations of known compounds with few toxic or side effects, which are useful for the treatment of this complex pathology.

It has now been found that the use of the acetyl L-carnitine, or a pharmaceutically acceptable salt thereof, in association with the biotin exerts a remarkable synergic effect on the reduction in insulin resistance, which characterizes the Type 2 diabetes mellitus.

Therefore, an object of the invention is the use of the acetyl L-carnitine, or a pharmaceutically acceptable salt thereof, in association with the biotin for the preparation of a medicament for the treatment of Type 2 insulin-resistant diabetes.

By pharmaceutically acceptable salt of the acetyl L-carnitine is meant any salt of this with an acid that does not give rise to undesirable toxic or side effects. These acids are well known to pharmacologists and to experts in pharmacy.

Non-limiting examples of these salts are the following: chloride, bromide, orotate, acid aspartate, acid citrate, citrate magnesium, acid phosphate, fumarate and acid fumarate, fumarate magnesium, lactate, maleate and acid maleate, mucate, acid oxalate, pamoate, acid pamoate, acid sulphate, phosphate glucose, tartrate, acid tartrate, tartrate magnesium, 2-amine ethanesulphonate, magnesium 2-amine ethanesulphonate, tartrate coline and trichloroacetate.

As stated above, neither suggestions nor mentions are made in the above-mentioned prior art literature regarding the use of the association according to the invention for the treatment of the Type 2 insulin-resistant diabetes. By reading the above-mentioned scientific literature, the person skilled in the art could not have arrived at the synergy among the compounds according to this invention without a big inventive effort.

In fact, this association shows an unexpected synergic effect, unpredictable on the basis of the knowledge of the use of both compounds, either alone or in association, and can be used as a suitable medicament for the treatment of the Type 2 insulin-resistant diabetes.

Though the daily dose to be administered, whether one single or multiple, is left to the doctor's judgment according to the weight, age and general condition of the patient, it has been found that the quantity of acetyl L-carnitine to be administered is 0.1 to 2 g/day, while the dose of biotin is 1 to 8 mg/day.

A preferred amount of the acetyl L-carnitine is 0.2 to 1 g/day, while of the biotin is 3 to 5 mg/day.

A more preferred amount of the acetyl L-carnitine is 0.3 g/day, while of the biotin is 4 mg/day.

The acetyl L-carnitine and the biotin, alone or associated, can be formulated with the excipient commonly used for the preparation of compositions for oral or parenteral administration, which are well known to the experts in pharmacology.

The invention claimed is:

1. A method for treating Type 2 insulin-resistant diabetes consisting of administering to a subject in need thereof acetyl L-carnitine or a pharmaceutically acceptable salt thereof in association with biotin, wherein the amount of acetyl L carnitine is 0.1 to 2 g/day and the amount of biotin is 1 to 8 mg/day; and treating Type 2 insulin-resistant diabetes in said subject in need thereof wherein the amount of acetyl L-carnitine to be administered is 0.2 to 1 g/day, while the amount of biotin is 3 to 5 mg/day.

2. The method according to claim 1, wherein said salt is selected from the group consisting of chloride, bromide, orotate, acid aspartate, acid citrate, citrate, magnesium citrate, acid phosphate, fumarate and acid fumarate, magnesium fumarate, lactate, maleate and acid maleate, mucate, acid oxalate, pamoate, acid pamoate, acid sulphate, glucose phosphate, tartrate, acid tartrate, magnesium tartrate, 2-aminoethansulphonate, magnesium 2-aminoethansulphonate, choline tartrate and trichloroacetate.

3. The method according to claim 1, wherein the amount of acetyl L-carnitine to be administered is 0.3 g/day, while the amount of biotin is 4 mg/day.

* * * * *